United States Patent [19]

Leupold et al.

[11] Patent Number: 4,481,146

[45] Date of Patent: Nov. 6, 1984

[54] PROCESS FOR THE PREPARATION OF AN ETHYL ESTER

[75] Inventors: Ernst I. Leupold, Neu-Anspach; Hans-Joachim Schmidt, Königstein; Knut Popp, Bad Soden am Taunus, all of Fed. Rep. of Germany

[73] Assignee: Hoechst Aktiengesellschaft, Frankfurt am Main, Fed. Rep. of Germany

[21] Appl. No.: 306,877

[22] Filed: Sep. 29, 1981

[30] Foreign Application Priority Data

Oct. 1, 1980 [DE] Fed. Rep. of Germany ....... 3037158

[51] Int. Cl.³ .......................... B01D 3/14; C11C 3/02; C07C 67/02
[52] U.S. Cl. ................................ 260/410.9 R; 203/38; 203/DIG. 6; 260/421; 560/248; 560/265
[58] Field of Search ..................... 203/DIG. 6, 99, 60, 203/61, 96, 38; 560/248, 265; 260/410.9 R, 421

[56] References Cited

U.S. PATENT DOCUMENTS

| | | | |
|---|---|---|---|
| 1,400,849 | 12/1921 | Backhaus | 560/265 |
| 1,939,116 | 12/1933 | Fuchs | 560/265 |
| 2,155,625 | 4/1939 | Von Retze | 560/265 |
| 2,274,061 | 2/1942 | Hawley | 560/265 |
| 3,914,290 | 10/1975 | Otsuki et al. | 203/DIG. 6 |
| 4,314,947 | 2/1982 | Hohenschutz | 203/DIG. 6 |

FOREIGN PATENT DOCUMENTS 1173089 12/1969 United Kingdom .
1394651 5/1975 United Kingdom .

Primary Examiner—Wilbur Bascomb
Attorney, Agent, or Firm—Curtis, Morris & Safford

[57] ABSTRACT

The invention relates to a process for the preparation of an ethyl ester from ethanol-containing mixtures of aliphatic alcohols, which comprises esterifying the alcohols with a carboxylic acid in the presence of an acid catalyst in a distilling column and separating in the same column the ethyl ester continuously from the ester mixture obtained. To this purpose, the alcohol mixture is introduced into the sump and the carboxylic acid is introduced into the column at a point located in the central part and the ethyl ester as well as the water formed during esterification are withdrawn continuously at the top of the column and the higher esters are withdrawn continuously at the sump.

2 Claims, 1 Drawing Figure

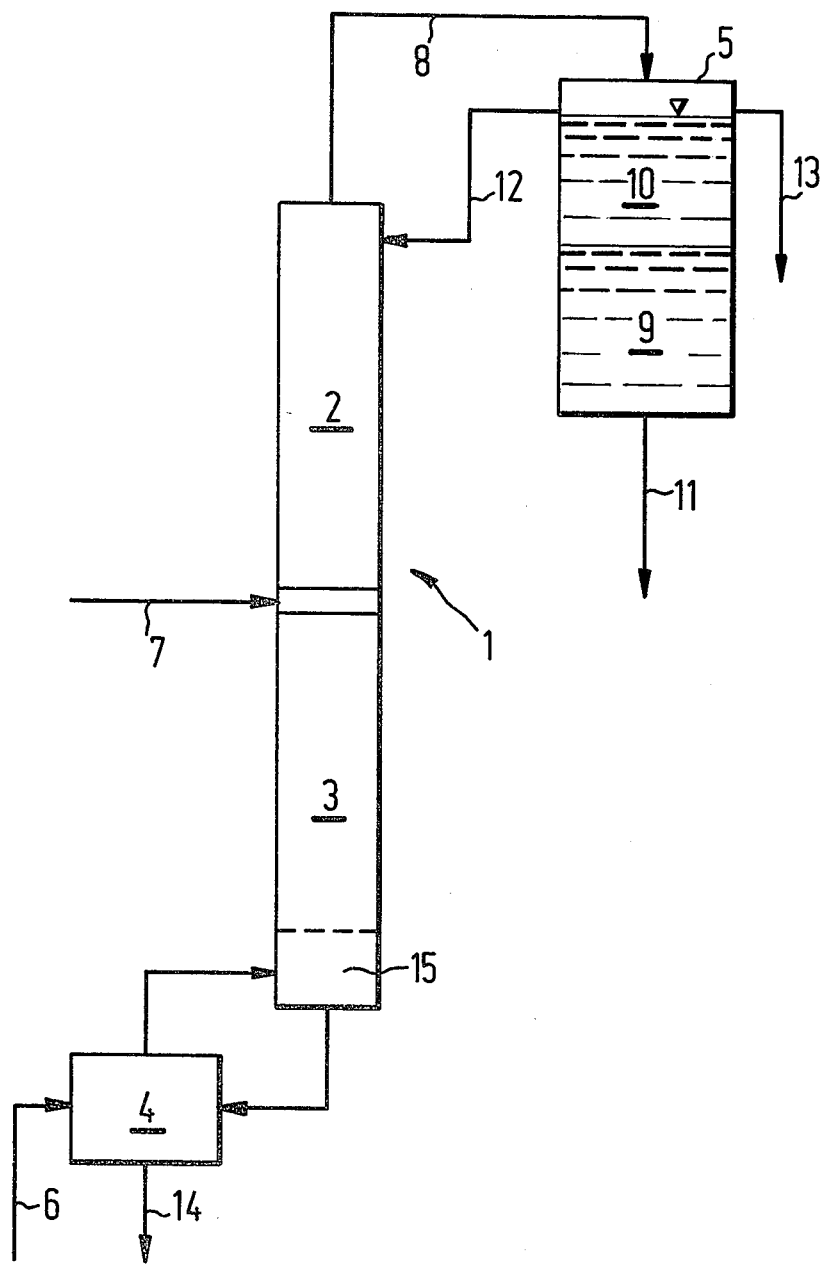

PROCESS FOR THE PREPARATION OF AN ETHYL ESTER

The present invention relates to a process for the preparation of an ethyl ester from ethanol-containing mixtures of aliphatic alcohols.

The CO-hydrogenation in the presence of heterogeneous catalysts according to German Offenlegungsschriften Nos. 2,628,463 and 2,748,097 yields among others mixtures of aliphatic alcohols, especially ethanol and various propanols and butanols. These alcohol mixtures may be separated from the other gaseous and liquid products obtained in CO-hydrogenation processes and be subsequently converted into a mixture of the corresponding esters by esterification with a carboxylic acid.

Ethyl esters, in particular ethyl acetate, if acetic acid has been used as the carboxylic acid, are important raw materials for the varnish and lacquer industries.

A process permitting the formation of an ethyl ester and its simultaneous separation from other esters in one column has not been known.

A process has now been found for the preparation of an ethyl ester from ethanol-containing mixtures of aliphatic alcohols, which comprises esterifying the alcohols with a carboxylic acid in the presence of an acid catalyst in a distilling column and separating in the same column the ethyl ester so formed continuously from the ester mixture obtained, the alcohol mixture being fed into the sump of the column and the carboxylic acid being fed into a point located in the central portion of said column and the ethyl ester as well as the water formed during esterification being withdrawn continuously at the top of the column and the heavier esters being withdrawn continuously at the sump.

Suitable for the esterification according to the present invention with simultaneous separation of the ethyl ester are all ethanol-containing mixtures of aliphatic alcohols with from 2 to 8 carbon atoms, which may contain, for example, in addition to ethanol, propanols, butanols, pentanols and hexanols as well as 2-ethylhexanol. A mixture of ethanol, propanols and butanols is particularly suitable.

If the mixture contains no ethanol, there is separated the ester of the alcohol which has the lowest boiling point.

The mixtures to be used may already contain esters in addition to the aliphatic alcohols, without perturbances being observed. For example, the reaction mixtures obtained according to German Offenlegungsschrift No. 2,628,463 contain ethyl acetate, which does not undergo a chemical modification in the process of the present invention, if the carboxylic acid used is acetic acid. However, further components, such as acetaldehyde and water, should have been separated previously, as they may induce side reactions or as they may result in an unsatisfactory yield.

Any carboxylic acids may be used generally for the esterification of the alcohol mixture, aliphatic carboxylic acids having from 2 to 8 carbon atoms, in particular acetic acid, being preferred, however.

The molar ratio of carboxylic acid to the sum of the alcohols may vary within wide limits, it ranges preferably from 1:1 to 5:1, particularly from 1.1:1 to 2.0:1.

The catalysts used are strong acids, preferred are $H_2SO_4$ and ion exchange resins having $SO_3H$ groups.

A preferred embodiment of the process according to the present invention is illustrated in the accompanying FIGURE representing a flow scheme and in the description referring thereto. The apparatus used consists of a column (1) having 10 bubble trays in the rectifying section (2) and in the stripping section (3), respectively, an evaporator (4) and a receiver (5). The alcohol mixture is conveyed to the evaporator (4) via the conduit (6), the carboxylic acid is fed to the column via the conduit (7) located between the rectifying section (2) and the stripping section (3). The head product of the column is conveyed to the receiver (5) by passing through the conduit (8), said head product forming two phases in the receiver, the lower of which (aqueous phase) (9) is withdrawn through the conduit (11). The upper (organic) phase (10) substantially consists of the desired ethyl ester. Part of this ester is recycled as reflux to the column by passing through the conduit (12), a second part is withdrawn via the conduit (13).

The carboxylic acid esters of the higher alcohols, however, are withdrawn from the evaporator (4) via the conduit (14) together with excess carboxylic acid.

If a liquid strong acid is used as the esterification catalyst, this acid is dissolved in the carboxylic acid and the resulting solution is fed to the column via the conduit (7).

If a heterogeneous acid catalyst is used, this is employed as dumped tower packing in the bottom part (15) of the column (1).

EXAMPLE 1

The example is carried out using the apparatus as illustrated in the FIGURE. The column (1) having 10 bubble trays in the rectifying section (2) and in the stripping section (3), respectively, has an inner diameter of 50 mm.

The electrically heated evaporator (4) is charged with 50 g/h of a mixture consisting of 14.1 weight % of ethyl acetate, 40.4 weight % of ethanol, 11.1 weight % of n-propanol, 11.2 weight % of n-butanol and 23.2 weight % of $H_2O$, at a sump temperature of 108° C.

50 g/h of acetic acid containing 0.1 weight % of $H_2SO_4$ is pumped into the column via the conduit (7) at a level above the tenth tray from below.

An upper organic phase (10) and a lower aqueous phase (9) are obtained in the receiver (5). Part of the upper phase containing 96.4 weight % of ethyl acetate, 0.6 weight % of ethanol, 3.0 weight % of $H_2O$ and less than 0.01 weight % of acetic acid is withdrawn via the conduit (12) at a rate of 43.5 g/h. The remainder is recycled via the conduit (11), at a reflux ratio of 25. The product withdrawn from the upper phase (10) contains more than 90% of the quantity of ethyl acetate, that may be prepared theoretically from the ethanol feed product; the lower phase (9) contains in addition to water 7.7 weight % of ethyl acetate and 3.8 weight % of ethanol. The head temperature of the column is 71° C.

A mixture consisting of 27.9 weight % of acetic acid n-propyl ester, 25.0 weight % of acetic acid n-butyl ester and 45.0 weight % of acetic acid is withdrawn continuously from the evaporator (4).

EXAMPLE 2

This example is carried out using the apparatus as illustrated in the FIGURE and in Example 1. The lower part (14) of the column contains 185 g of a commercial cation exchanger resin containing $SO_3H$ groups.

To the evaporator (4) there is fed, at a sump temperature of 115° C., 55 g/h of a mixture consisting of 40.2 weight % of ethanol, 11.5 weight % of n-propanol, 11.5 weight % of n-butanol and 36.8 weight % of $H_2O$.

Acetic acid is fed to the column via the conduit (7) at a point above the tenth tray from below, at a rate of 50 g/h.

At a head temperature of 71° C. the upper organic phase (10) of the distillate consists of 97.0 weight % of ethyl acetate, 2.5 weight % of $H_2O$, 0.5 weight % of ethanol and less than 0.01 weight % of acetic acid. The reflux ratio is 25.

The aqueous phase (9) contains 6.9 weight % of ethyl acetate and 2.3 weight % of ethanol.

The sump product withdrawn via the conduit (13) contains 36.1 weight % of acetic acid, 22.0 weight % of acetic acid n-propyl ester and 36.5 weight % of acetic acid n-butyl ester.

What is claimed is:

1. A process for the preparation of an ethyl ester from an ethanol containing mixture of aliphatic alcohols, which comprises:

feeding a mixture of aliphatic alcohol to distillation column at a point located in the sump portion of said distillation column;

feeding carboxylic acid to the distillation column at a point located near the middle of said distillation column;

esterifying in said distillation column said mixture of aliphatic alcohol with said carboxylic acid at a molar ratio of from 1.1:1 to 2.0:1 acid to alcohol in the presence of an acid catalyst to form water and a mixture of esters containing ethyl ester and heavier esters;

continuously separating the ethyl ester so formed in the distillation column from said mixture of esters;

continuously withdrawing the water and ethyl ester formed through the upper portion of said distillation column; and continuously withdrawing the heavier esters formed through the sump of said distillation column.

2. The process of claim 1 wherein said acid catalyst is $H_2SO_4$ or an ion exchanger resin containing $SO_3H$ groups.

* * * * *

UNITED STATES PATENT AND TRADEMARK OFFICE
CERTIFICATE OF CORRECTION

PATENT NO. : 4481146

DATED : November 14, 1984

INVENTOR(S) : Leopold et al.

It is certified that error appears in the above-identified patent and that said Letters Patent is hereby corrected as shown below:

Column 4 (claim 1), lines 1, 8 and 9, change "alcohol" to --alcohols--

Column 2, line 50, change "(12)" to --(13)--

Column 2, line 51, change "(11)" to --(12)--

Column 2, line 67, change "(14)" to --(15)--

Column 3, line 16, change "(13)" to --(14)--

Signed and Sealed this

Seventh Day of May 1985

[SEAL]

Attest:

DONALD J. QUIGG

*Attesting Officer*   *Acting Commissioner of Patents and Trademarks*